(12) United States Patent
Riechers et al.

(10) Patent No.: US 9,400,243 B2
(45) Date of Patent: Jul. 26, 2016

(54) DISPOSABLE SENSOR HEAD AND DISPOSABLE CONTAINER

(75) Inventors: Daniel Riechers, Regensburg (DE); Christian Grimm, Heilbad Heilingenstadt (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 147 days.

(21) Appl. No.: 14/113,342

(22) PCT Filed: May 5, 2012

(86) PCT No.: PCT/EP2012/001942
§ 371 (c)(1),
(2), (4) Date: Oct. 22, 2013

(87) PCT Pub. No.: WO2012/152423
PCT Pub. Date: Nov. 15, 2012

(65) Prior Publication Data
US 2014/0054186 A1    Feb. 27, 2014

(30) Foreign Application Priority Data

May 10, 2011 (DE) .......................... 10 2011 101 107

(51) Int. Cl.
| | |
|---|---|
| *G01N 21/05* | (2006.01) |
| *B65D 25/54* | (2006.01) |
| *G01N 21/03* | (2006.01) |
| *G01N 21/85* | (2006.01) |
| *C12M 1/34* | (2006.01) |

(52) U.S. Cl.
CPC ............... *G01N 21/05* (2013.01); *B65D 25/54* (2013.01); *C12M 41/00* (2013.01); *G01N 21/031* (2013.01); *G01N 21/85* (2013.01)

(58) Field of Classification Search
USPC ................ 356/244, 246; 435/292.1; 206/305; 422/82.05
See application file for complete search history.

(56) References Cited

U.S. PATENT DOCUMENTS 3,208,344 A * 9/1965 Staunton ........................ 248/466
4,066,361 A * 1/1978 Achter .............................. 356/41

(Continued)

FOREIGN PATENT DOCUMENTS

| DE | 27 09 887 | 9/1977 |
| DE | 198 43 553 | 4/2000 |

(Continued)

OTHER PUBLICATIONS

International Search Report of Jul. 12, 2012.

(Continued)

*Primary Examiner* — Sang Nguyen
(74) *Attorney, Agent, or Firm* — Gerald E. Hespos; Michael J. Porco; Matthew T. Hespos

(57) ABSTRACT

A disposable sensor head for an optical sensor has a central body (12) with an axial through-channel (20) closed by a transparent viewing disk (14) oriented transversely with respect to its longitudinal direction, and a circumferential fastening flange (22), by which the central body is fastenable in a sealing fashion on a wall of a flexible container (62) so that the through-channel (20) passes through the wall. The through-channel (20) forms in one section an open flow chamber (34) that is bounded on one side by the viewing disk (14) and on the other side by a reflector disk (16) arranged opposite the viewing disk (14).

8 Claims, 2 Drawing Sheets

(56) References Cited

U.S. PATENT DOCUMENTS

| | | | |
|---|---|---|---|
| 4,099,870 A | | 7/1978 | Luzzi |
| 4,256,696 A | * | 3/1981 | Soodak .................. 422/72 |
| 4,413,923 A | * | 11/1983 | Wright .................. 404/11 |
| 4,464,936 A | * | 8/1984 | McIntire et al. .............. 73/705 |
| 5,781,306 A | * | 7/1998 | Hartig et al. .................. 356/436 |
| 5,794,647 A | * | 8/1998 | Denmark et al. ........ 137/315.24 |
| 6,154,441 A | * | 11/2000 | Sandstrom et al. ........... 369/282 |
| 2002/0196435 A1 | * | 12/2002 | Cohen et al. .................. 356/246 |
| 2007/0023208 A1 | * | 2/2007 | Jung et al. .................. 177/50 |
| 2007/0132991 A1 | * | 6/2007 | Alspach et al. ............... 356/246 |
| 2007/0132992 A1 | * | 6/2007 | Alspach et al. ............... 356/246 |
| 2007/0157748 A1 | | 7/2007 | Baumfalk et al. |
| 2008/0171383 A1 | | 7/2008 | Selker et al. |
| 2009/0075362 A1 | | 3/2009 | Baumfalk et al. |
| 2010/0035337 A1 | * | 2/2010 | Bahnemann et al. ...... 435/292.1 |
| 2013/0039810 A1 | * | 2/2013 | Riechers .................. 422/82.05 |

FOREIGN PATENT DOCUMENTS

| | | |
|---|---|---|
| DE | 10 2006 022 307 | 11/2001 |
| DE | 10 2006 001 610 | 7/2007 |
| WO | WO 2010145747 A1 * | 12/2010 |

OTHER PUBLICATIONS

Biotechnology and Bioengineering, vol. 99, No. 2, 2008, pp. 302-313.

Biotechnology Progress 2003, vol. 19, No. 6, pp. 1816-1821.

* cited by examiner

DISPOSABLE SENSOR HEAD AND DISPOSABLE CONTAINER

BACKGROUND

1. Field of the Invention

The invention relates to a disposable sensor head for an optical sensor, comprising a central body having an axial through-channel closed by a transparent viewing disk oriented transversely with respect to its longitudinal direction, and a circumferential fastening flange, by means of which the central body is fastenable in a sealing fashion on a wall of a flexible container in such a way that the through-channel passes through the wall. The invention furthermore relates to a disposable container having a flexible wall and at least one disposable sensor head of an optical sensor, wherein the sensor head comprises a central body having an axial through-channel closed by a transparent viewing disk oriented transversely with respect to its longitudinal direction, and a circumferential fastening flange and by means of the fastening flange the central body is fastened in a sealing fashion on the flexible wall in such a way that the through-channel passes through the wall.

2. Description of the Related Art

Disposable sensor heads and disposable containers are known from 10 2006 001 610 B4.

Particularly in the pharmaceutical and biotechnological industries, for the production, storage and use of liquids and gases (referred to together as fluids below), disposable containers having flexible walls are used instead of the previously more commonly used rigid tanks and cylinders. Such disposable containers will be referred to here as bags for brevity. As in the case of rigid containers, the monitoring of a very wide variety of parameters of the fluids in the bags is necessary. To this end, it is known from the aforementioned document to use optical sensors passing through the bag wall. For reasons of costs as well as sterilization, the sensor head, i.e. the part of the sensor forming the optical contact with the fluid to be monitored, is formed as a disposable element which is delivered to the customer firmly connected to the bag and sterile, and is disposed of together with the bag after use of the latter. In this case, it is desirable to accommodate reusable, expensive and/or non-sterilizable components, for example light sources, electronic evaluation units, etc. in a couplable module, and as far as possible to accommodate only robust, inexpensive, sterilizable and easily disposable elements in the disposable sensor head.

In one of the exemplary embodiments disclosed in DE 10 2006 001 610 B4, the central body firmly clamped to its fastening flange on the bag wall by means of a backing piece comprises a central through-bore. The latter forms a through-channel which has an inlet lying outside the bag and an outlet lying inside the bag, and therefore passes through the bag wall. A volume flow through the through-channel is prevented by a viewing disk, which seals the channel. The viewing disk is transparent, which in the scope of the present description is respectively to be understood in relation to the measurement to be carried out and means a sufficient transmissivity for light of the wavelengths required for the measurements in question. In the known embodiment, this viewing disk is applied on the outlet of the through-channel and closes the latter in the shape of a dome. It forms the optical interface between a fluid inside the bag and a glass fiber, which is arranged inside the channel and inputs illumination light and outputs detection light.

Such a sensor head is suitable for carrying out back-scattering, fluorescence and phosphorescence measurements. Transflection measurements, such as may be used particularly in the scope of NIR spectroscopy (near-infrared spectroscopy), cannot be carried out with the known sensor head.

It is an object of the present invention to further refine the known disposable sensor head, in such a way that transflection measurements, in particular NIR spectroscopy measurements, can be carried out with it.

It is another object of the present invention to provide sensor-equipped bags which permit transflection examination, in particular an NIR spectroscopy examination, of the bag contents.

SUMMARY OF THE INVENTION

The object mentioned first is achieved in that the through-channel forms in one section an open flow chamber, which is bounded on one side by the viewing disk and on the other side by a reflector disk arranged opposite the viewing disk.

The object also is achieved in that the through-channel flows into an open flow chamber of the sensor head, which chamber is positioned inside the container and is bounded in the direction of the container exterior by the viewing disk and in the direction of the container interior by a reflector disk arranged opposite the viewing disk.

The basic concept of the present invention is to make the through-channel open into a transflection flow chamber, which is contained in the central body of the sensor head and can be regarded as an end section of the flow channel. Other than as is known in the prior art, the flow channel is therefore used not only to input and output light but has an input and output section for light which lies outside the bag in the final assembled state and, inside the bag in the final assembled state, an interaction section for defined interaction between light and bag content. To this end, the viewing disk sealing the through-channel is set back from the channel outlet, the channel outlet itself is placed forward in the direction of the bag interior and closed by a reflector disk, and the resulting chamber between the viewing and reflector disks is open to the bag interior so that the fluid of the bag interior can flow through it. Light from a light source is therefore delivered through the input and output section of the through-channel, shines through the viewing disk, interacts with the medium in the flow chamber, is reflected and/or scattered at the reflector disk, depending on the particular configuration thereof, interacts with the medium in the flow chamber again, shines through the viewing disk again and is output through the input and output section of the through-channel for suitable detection.

So that the fluid contained in the flow chamber is representative of the total bag content, good flow through the flow chamber is necessary. To this end, it is preferably provided that flow chamber comprises at least two lateral openings arranged between the viewing disk and the reflector disk. Favorably, the openings are selected to be as large as possible. Preferably, they occupy the majority of the wall of the through-channel between the viewing disk and the reflector disk, and are separated from one another merely by narrow webs.

In a preferred refinement of the invention, it is provided that the central body comprises, on the side of the viewing disk facing away from the reflector disk, a coupling device for reversible coupling of an optoelectronic sensor module. An optoelectronic sensor module is intended here to mean a component which comprises a light source, a detector unit and suitable light guide elements. The light guide elements may be fiber-optic, but preferably beam-optic in nature. Particularly in the field of NIR spectroscopy measurements, fiber-optic light-guide elements may entail problems in respect of transparency, dispersion, aperture, losses at fiber bends, etc. Preferably, therefore, the optoelectronic sensor module comprises an NIR light source, a purely or at least predominantly beam-optic illumination beam path consisting of mirrors and optionally lenses, a likewise purely or at least predominantly beam-optic detection beam path and an NIR detector, in particular an NIR spectrometer, the spectrometer entry of which may readily contain fiber-optic elements. Owing to the beam-optic input and output of the light, positionally stable coupling between the sensor head and the optoelectronic sensor module is necessary. This requirement is satisfied by the aforementioned refinement of the invention owing to the direct coupling with the central body. Corresponding coupling standards are known to the person skilled in the art, for example from microscopy.

The central body by no means necessarily needs to be constructed in one part. Rather, it is readily possible and often advantageous for the central body to be constructed in a plurality of parts and to comprise a main body and at least one further central body component. This may, for example, be carried out in such a way that the viewing disk is held clamped in a sealing fashion between the main body and an end side of a clamping ring. The clamping ring may for example be fastened on the main body as a threaded ring, in the manner of a circlip, by latching or in a similar way. Its purpose is to press the viewing disk against a projection, preferably provided with a seal, of the through-channel, in order on the one hand to hold it and on the other hand to seal it.

In a refinement of this embodiment, it is provided that the clamping ring comprises, on its end side facing away from the viewing disk, the coupling device for reversible coupling of the optoelectronic sensor module. The clamping ring is therefore assigned a double function, namely on the one hand to hold and seal the viewing disk, as described above, and on the other hand as an adapter for the optoelectronic sensor module.

A further embodiment of a central body constructed in a plurality of parts, which may be implemented as an alternative or preferably in addition to that mentioned above, consists in that the reflector disk is fixed on an adjustment plate which is set at an adjustable distance from the viewing disk on the main body. This embodiment has the particular advantage that the optical path for the transflection measurement can be adjusted according to the requirement of the individual case. For example, the adjustment plate may be formed as a body having an external screw thread, which can be screwed into an internal screw thread at the exit of the through-channel. More favorable from cost aspects, and in the majority of practically relevant cases entirely sufficient, is a variant in which the adjustment plate and the main body comprise corresponding latching grooves and latching ribs. For example, the adjustment plate may be provided with a circumferential latching groove or a circumferential latching rib, which respectively snap-fits into one of a plurality of corresponding latching grooves or latching ribs, arranged mutually parallel, in the inner wall of the through-channel near the exit. In this way, the sensor-head geometry defines a plurality of fixed positions for the adjustment plate, one of which may be selected during mounting of the sensor head. Of course, this type of fixing of the adjustment plate is also possible in principle when there is only one predetermined position.

As already mentioned in the introduction, the main field of use of the disposable sensor head according to the invention consists in its use together with disposable containers having flexible walls, that is to say with the bags explained in the introduction. Correspondingly, bags having an integrated disposable sensor head according to the invention are a separate component of the present application, in which case each of the previously explained embodiments and refinements of the sensor head according to the invention may be employed.

The fastening of the disposable sensor head according to the invention on the bag, in order to provide a disposable container according to the invention, may be carried out in various ways. In particular, the fastening flange may be welded, adhesively bonded, and/or clamped by means of an additional backing piece to the wall.

Other features and advantages of the present invention may be found in the following particular description and the drawings.

DETAILED DESCRIPTION OF PREFERRED EMBODIMENTS

Identical references in the figures refer to elements which are the same or similar.

Figure 1:
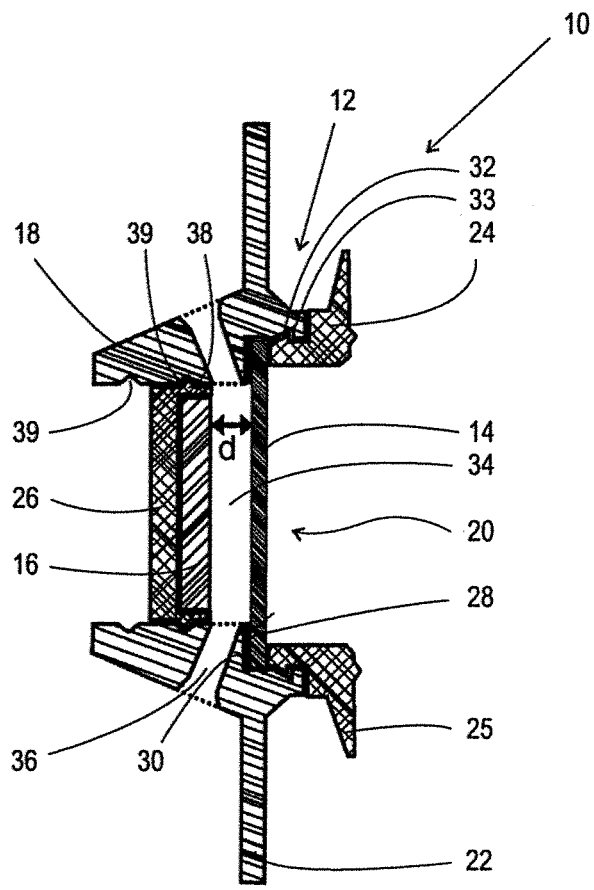
FIG. 1 shows a sectional representation of the sensor head according to the invention.

FIG. 1 shows a sectional representation through a sensor head 10 according to the invention. Functional components of the sensor head 10 are its central body 12, a viewing disk 14 and a reflector disk 16. In the present exemplary embodiment, the central body 12 is formed in three parts and comprises, in particular, a main body 18 having a central through-channel 20 and a fastening flange 22, a clamping ring 24 by which the viewing disk 14 is retained, and an adjustment plate 26 which carries the reflector disk 16. The preferred material for at least the main body is a weldable hard plastic.

By means of the fastening flange 22, the main body 18 can be set on a wall of a container, in particular a flexible bag 62, as shown by way of example in FIG. 4 which will be explained below. In this case, the fastening flange 22 may be adhesive-bonded or welded to the container wall. As an alternative to this, it may also be set by means of one or more backing pieces, for example by screwing, clamping, latching, etc. The fastening flange 22 therefore forms a section boundary between an inner region, lying inside the container in the final assembled state, and an outer region of the sensor head, lying outside the container in the final assembled state. The through-channel 20 passes through both regions.

In the embodiment shown, approximately at the height of the fastening flange 22, the through-channel 20 has a projection 28 on which a seal 30, for example a flat or liquid seal, is applied. The viewing disk 14, which has a sufficient transparency for the light required in the scope of the optical measurement respectively to be used, rests on the seal 30. In the preferred variant of NIR spectroscopic measurement, a viewing disk consisting of quartz or sapphire has proven favorable. The viewing disk 14 is clamped against the seal 30 by means of the clamping ring 24, the intrinsic elasticity of the seal 30 permanently sustaining the clamping force. In the embodiment shown, the clamping ring 24 has a circumferential latching rib 32, which latches into a corresponding latching groove 33 in the main body 18. This presupposes a corresponding elasticity of the clamping ring 24 and/or of the main body 18, although this is satisfied when one or both of the elements mentioned, as is preferably provided, are formed from a corresponding plastic. As an alternative to the embodiment shown, the clamping ring could, for example, also be provided with an external screw thread which can be screwed into an internal screw thread of the main body.

Formed on the clamping ring 24, at its end facing away from the viewing disk 14, there is a coupling structure 25 which, in the embodiment shown, corresponds to the tri-clamp standard known in technical circles. As described in more detail below in connection with FIG. 4, the coupling structure 25 is used for coupling an optoelectronic sensor module 40.

In the embodiment shown, the viewing disk 14 forms the boundary between an inner region and an outer region of the through-channel 20.

The inner region of the through-channel 20, or of the main body 18, can be subdivided into two subregions. The subregion lying closest to the viewing disk 14 is configured as a flow chamber 34. To this end, lateral openings 36 passing through the main body 18 are provided, which in the final assembled state allow fluid exchange between the flow chamber 34 and the container interior. The flow chamber is closed by the reflector disk, which lies opposite the viewing disk 14 and essentially parallel thereto, and which is in turn fastened on an adjustment plate 26, for example adhesively bonded thereto. In the embodiment represented, the adjustment plate 26 comprises a circumferential latching rib 38 which is latched into one of two latching grooves 39, corresponding therewith, in the inner wall of the through-channel 20 formed by the main body 18. The distance, denoted in FIG. 1 by "d", between the reflector disk 16 and the viewing disk 14 forms the height of the flow chamber 34, which in the embodiment shown may be increased by one increment by latching the adjustment plate 26 into the second of the latching grooves 39 represented. Of course, embodiments with only one latching groove 39, with more than two latching grooves 39 and with other fastening means are also possible, for example an external screw thread on the adjustment plate 26, which can be screwed into an internal screw thread of the main body 18. It is, of course, also possible to fix the reflector disk 16 permanently on the main body 18 in a way which is not adjustable.

Figure 2:
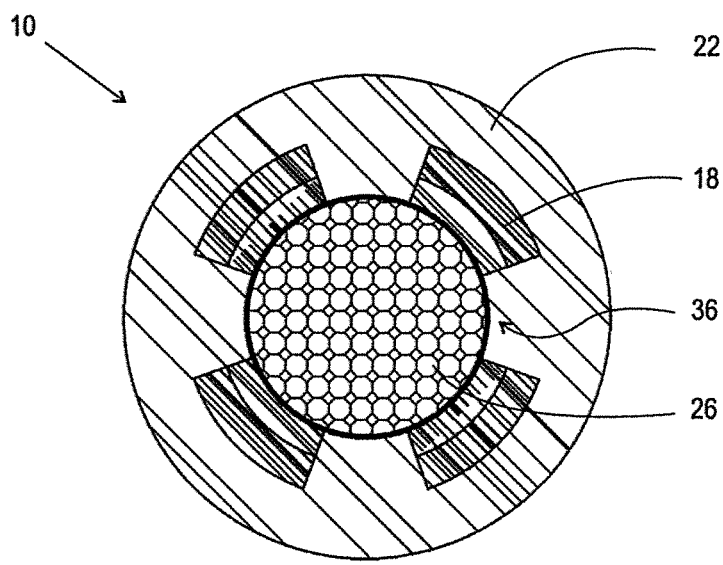
FIG. 2 shows a plan view of the sensor head according to the invention along the viewing line arrow II in FIG. 1.

FIG. 2 shows a plan view of the sensor head of FIG. 1 along the viewing arrow II, reference being made to the comments above for explanation.

Figure 3:
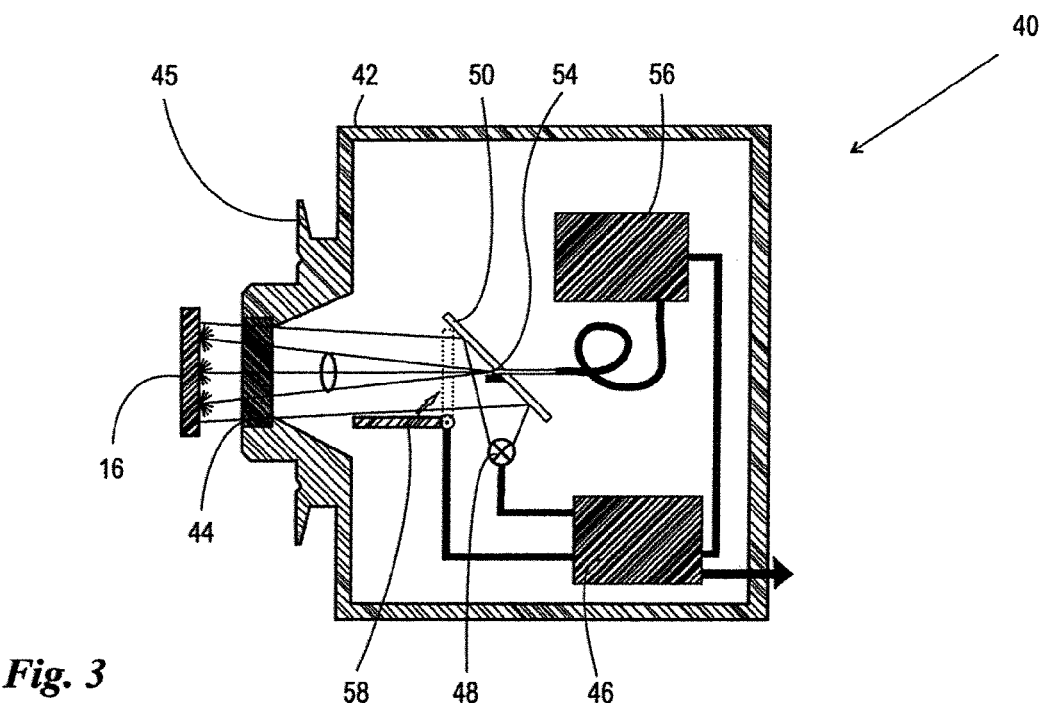
FIG. 3 shows an optoelectronic sensor module for coupling on the sensor head of FIGS. 1 and 2, as well as the reflector plate of the sensor head of FIGS. 1 and 2 to illustrate an exemplary beam path.

FIG. 3 shows a highly schematized sectional representation of an optoelectronic sensor module, which together with the sensor head of FIGS. 1 and 2 forms an optical sensor. For illustration of a preferred beam path, the reflector disk 16 of the sensor head 10 is also represented in addition to the optoelectronic sensor module 40. The optoelectronic sensor module 40 comprises a preferably dust- and liquid-tight housing 42. Formed in the wall of the housing 42, there is an optical window 44 which has sufficient transparency in the respectively required spectral range for the intended measurement. Particularly in the preferably used near-infrared range (NIR), windows consisting of quartz or sapphire may be used. The optical window 44 is enclosed by a coupling structure 45, which corresponds with the coupling structure 25 of the sensor head 10, i.e. in the present example it is configured according to the tri-clamp standard. Of course, it is also possible to use any other type of coupling which, in particular, ensures rigid coupling between the optoelectronic module 40 and the sensor head 10. Screw and bayonet coupling systems may be mentioned purely by way of example.

Rigid coupling becomes particularly important in the preferred cases of free-beam input and output of light respectively to and from the sensor head. Such a case is outlined in FIG. 3. A light source 48 powered by an electrical supply unit 46, and in particular with an emission spectrum in the NIR, generates illumination light which is guided to the optical window 44 by beam optics, in the case represented by means of a deflection mirror 50, and shines through it. The illumination light strikes the reflector disk 16, which is preferably formed as a Lambertian scattering disk but may also be configured in a different way, for example as a mirror. The light cast back by the reflector disk 16 passes through the optical window 44 once more (this time in the opposite direction) and is received in the solid angle 52 to the numerical aperture of the of the fiber-optic entry 54 of a spectrometer 56. This structure allows a transflection measurement of a medium which lies between the optical window 44 and the reflector disk 16. In the final assembled state, the flow chamber 34 of the sensor head 10 lies at precisely this position.

In addition to the aforementioned components, a reflection flap 58 is also provided in FIG. 3, which may be folded into the illumination beam path for calibration purposes so that the light of the light source 48 is cast onto the reflection flap by means of the mirror 50 and can be reflected, or scattered, therefrom to the entry 54 of the spectrometer 56. This direct measurement of the illumination light may be used to create a reference with which subsequently measured detection light of a transflection measurement can be compared.

Figure 4:
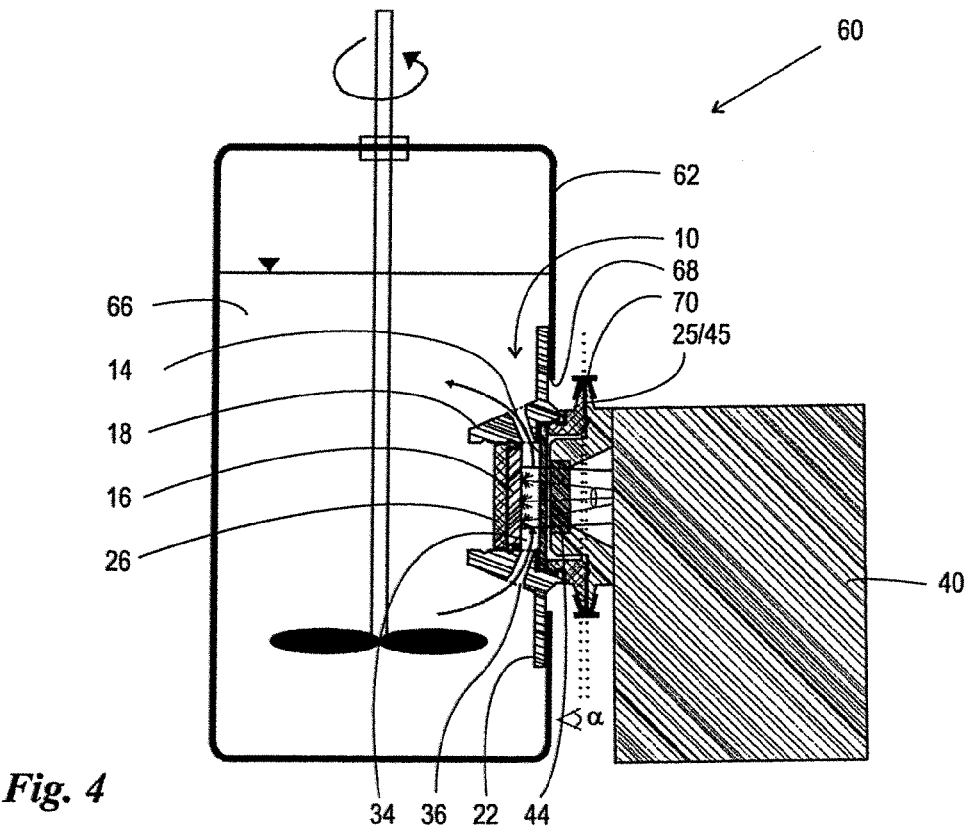
FIG. 4 shows a disposable container according to the invention, comprising a bag, a sensor head according to the invention and an optoelectronic sensor module coupled to the latter.

FIG. 4 shows the final assembled state of a disposable container 60 according to the invention. The container consists of a flexible bag 62, which is filled with fluid 64. In the embodiment shown, a stirring mechanism 66 extending into the interior of the bag 64 is furthermore provided, which maintains a permanent flow inside the mediums 64. The sensor head is fitted in the manner already described into a hole 68 through the wall of the bag 62. In particular, in the embodiment shown, it is welded with the outer side of its fastening flange 22 onto the inner wall of the bag 62. The fluid 64 flows through the flow chamber 34 via its openings 36, the stirring mechanism 66 promoting the flow of "fresh" fluid through so that a measurement carried out on the volume of the flow chamber 34 can be assumed to be representative of the entire bag content. The optoelectronic sensor module 40 is coupled to the outer region of the sensor head 10, the tri-clamp coupling structures 25/45 being held together in a standardized way by a clamp 70. In the preferred embodiment represented in FIG. 4, the coupling structures 25/45 are configured in such a way that the optical window 44 is not parallel to the viewing disk 14, but assumes a small angle α, which preferably lies between 1 degree and 3 degrees, particularly preferably 2 degrees. In this way, errors which may result from reflection of the illumination light on the viewing disk 14 can be avoided.

Naturally, the embodiments discussed in the particular description and shown in the figures merely constitute illustrative exemplary embodiments of the present invention. A wide range of possible variants are available to the person skilled in the art. In particular, the structure of the optoelectronic sensor module may be technically adapted to the respectively intended measurement method.

The invention claimed is:
1. A disposable sensor head for an optical sensor, comprising:
 a central body (12) having:
  a main body (18) forming an axial through-channel (20)

a transparent viewing disk (14) extending across and closing the axial through channel (20) and oriented transversely with respect to an axial direction of the axial through-channel (20), a clamping ring (24) engaged with the main body (18) and securely holding the transparent viewing disk (14) against the main body (18) and across the axial through channel (20), a circumferential fastening flange (22) extending out on the main body (18) and by which the central body is fastenable in a sealing fashion on a wall of a flexible container (62) in such a way that the through-channel (20) passes through the wall, a reflector disk (16) mounted to the main body (18) in a position spaced from and opposed to the transparent viewing disk (14), and an open flow chamber (34) passing through the main body (18) at a position so that the open flow chamber (34) is bounded on one side by the viewing disk (14) and on the other side by a reflector disk (16) arranged opposite the viewing disk (14).

2. The sensor head of claim 1,
wherein
the flow chamber (34) comprises at least two lateral openings (36) arranged between the viewing disk (14) and the reflector disk (16).

3. The sensor head of claim 1,
wherein
the central body (12) comprises, on a side of the viewing disk (14) facing away from the reflector disk (16), a coupling device (25) for reversible coupling of an optoelectronic sensor module (40).

4. The sensor head of claim 3,
wherein
the clamping ring (24) comprises, on its end side facing away from the viewing disk (14), the coupling device (25) for reversible coupling of the optoelectronic sensor module (40).

5. The sensor head of claim 4,
wherein the reflector disk (16) is fixed on an adjustment plate (26) that is set at an adjustable distance from the viewing disk (14) on the main body (18).

6. The sensor head of claim 5,
wherein
the adjustment plate (26) and the main body (18) comprise corresponding latching grooves (39) and latching ribs (38).

7. A disposable container having a flexible wall and at least one disposable sensor head (10) of an optical sensor, wherein the sensor head (10) comprises a central body (12) having:

a main body (18) forming an axial through-channel (20), a transparent viewing disk (14) extending across and closing the axial through channel (20) and oriented transversely with respect to an axial direction of the axial through-channel (20), a clamping ring (24) engaged with the main body (18) and securely holding the transparent viewing disk (14) against the main body (18) and across the axial through channel (20), a circumferential fastening flange (22) extending out on the main body (18) and fastening the central body in a sealing fashion on the flexible wall in such a way that the through-channel (20) passes through the wall, a reflector disk (16) mounted to the main body (18) in a position spaced from and opposed to the transparent viewing disk (14), and an open flow chamber (34) of the sensor head (10) passing through the main body (18) at a position so the open flow chamber (34) is positioned inside the container and is bounded in a direction of the container exterior by the viewing disk (14) and in a direction of the container interior by a reflector disk (16) arranged opposite the viewing disk (14).

8. The disposable container of claim 7,
wherein
the fastening flange (22) is welded, adhesively bonded, or clamped by of an additional backing piece to the wall.

* * * * *